US00PP07937P

United States Patent [19]

Hanes

[11] Patent Number: Plant 7,937

[45] Date of Patent: Aug. 11, 1992

[54] AMERICANA CHERRY ROSE

[75] Inventor: Mitchell Hanes, Morgan Hill, Calif.

[73] Assignee: Goldsmith Seeds, Inc., Gilroy, Calif.

[21] Appl. No.: 656,708

[22] Filed: Feb. 19, 1991

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

A new and distinctive Geranium cultivar particularly distinguished by its rose red colored semi-double flowers and its vigorous fast-rooting growth habit.

1 Drawing Sheet

BACKGROUND OF THE NEW PLANT

The present invention comprises a new and distinct cultivar of Geranium, botanically known as *Pelargonium hortorum* Bailey. The new cultivar is propagated from a seedling resulting from the cross of a breeding line with rose red semi-double flowers and a pollen parent breeding line with a purple red single flower.

This geranium cultivar is a product of a planned breeding program intended to create new Geranium cultivars with rose red colored flowers, semi-double flower form, green foliage, vigorous growth and superior cutting productivity.

The new cultivar was created in 1988 in Gilroy, Calif. and has been repeatedly asexually reproduced by cuttings in Gilroy, Calif. and Guatemala over a two year period. It has also been trialed at Okemos, Mich. It has been found to retain its distinctive characteristics through successive propagations; and this novelty appears to be firmly fixed.

DESCRIPTION OF THE DRAWING

This new Geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVAR

The following detailed description set forth the distinctive characteristics of this geranium cultivar. The data which defines these characteristics were collected from asexual reproductions carried out by Goldsmith Seeds, Inc. in Gilroy, Calif. The plant history was taken on 36 week old plants, blossomed under natural light in a greenhouse and color readings were taken in the greenhouse on May 29, 1990 at 2:00 p.m. under ambient light. Color references are primarily to The R.H.S. Colour Chart of The Royal Horticultural Society of London, England.

THE PLANT

Classification:

*Botanical.*—*Pelargonium hortorum* Bailey.

*Commercial.*—Zonal Geranium.

Form: Compact bush with round habit.

Height: Eleven to fourteen cm., as a 5½ inch pot plant, excluding blooms.

Growth: Strong, and fast-rooting.

Strength: Floriferous plant that has good shipping ability as rooted or unrooted cuttings.

Foliage: Abundant quantity.

Leaves:

*Size.*—Diameter about 7.5 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate, 3 to 4.5 cm. long.

*Color.*—Upper side: Green with a darker green zone. Underside: Lighter green color with out zone. Ribs and veins not prominently different from upper surface.

Petioles: About 5.5 to 7.0 cm. in length.

THE BUD

Size:

*Diameter.*—about 8 mm.

*Length.*—about 1.2 cm to 1.5 cm. at time of bud opening.

Shape: Pointed ovoid.

Color: Of petals when sepals first divide, R.H.S. 57-A.

Sepals: Five in number, flat behind petals. Pointed linear lanceolate, R.H.S. 143-C in an open flower.

THE FLOWER

Blooming habit: Continuous throughout the year.

Size: Approximately 4.2 cm. diameter, 1.1 cm. deep, irregularly radially symmetrical.

Form: Cup-shaped when bloom first opens, later flattening to shallow cup shape with maturity.

Petals: Five imbricate outer petals, 1.9–2.0 cm. wide and approximately 2.1 cm. long, 1 to 5 inner smaller petaloids of varying shape. Both the outer petals and inner petaloids are a rose shade of red R.H.S. 57-A with a white tip at the proximal end. Veins not different from the interveinal regions. Color changing little with age. Underside of petals lighter. Petals and petaloids soft and satiny.

Pedicel: Approximately 2.7–3.0 cm. in length.

Persistence: Nonshattering flower.

INFLORESCENCE

Type: An umbel composed of approximately 25 flowers, erect or laterally ascending.

Peduncle: Approximately 9–10 cm. in length.

REPRODUCTIVE ORGANS

Stamens:

*Anthers.*—Seven — nine positioned below the mature stigma, dull red prior to anthesis.

*Filaments.*—White near base and mid length, graduating to dull red near anther.

Pollen.—Orange in color.

Pistil:

*Number.*—One.

*Length.*—Approximately 8 mm.

Stigma: Five (sometimes six) linear lobes of near equal length, curling back toward ovary, purplish-red.

Style:

*Length.*—About 4 mm., color: purplish-red.

Ovaries: At anthesis, densely pubescent with white hairs, oblong. Green drying to a light brown at maturity.

Fruit: Partially fertile.

I claim:

1. A new and distinct cultivar of Geranium substantially as herein shown and described, characterized by its green foliage with faint zonation, rose red colored semi-double flowers on large umbels, the plant being fast-rooting and having a vigorous round bush growth habit.

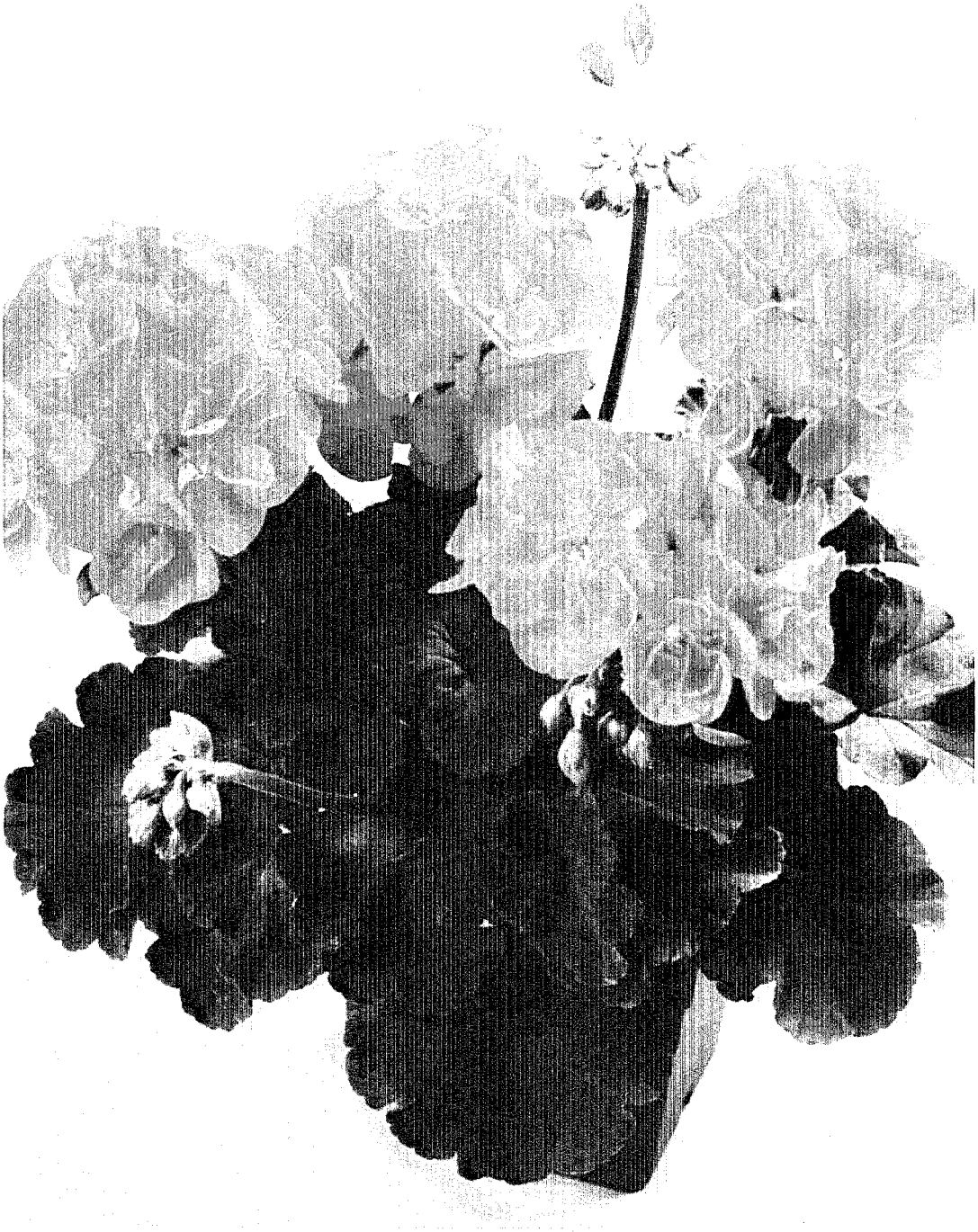

* * * * *